US008689788B2

(12) United States Patent
Rabi

(10) Patent No.: US 8,689,788 B2
(45) Date of Patent: Apr. 8, 2014

(54) OXYGENATION PROCEDURES FOR NEWBORNS AND DEVICES FOR USE THEREIN

(75) Inventor: Yacov Rabi, Calgary (CA)

(73) Assignee: UTI Limited Partnership, Calgary (CA)

( * ) Notice: Subject to any disclaimer, the term of this patent is extended or adjusted under 35 U.S.C. 154(b) by 497 days.

(21) Appl. No.: 12/937,180

(22) PCT Filed: Mar. 12, 2009

(86) PCT No.: PCT/IB2009/005452
§ 371 (c)(1),
(2), (4) Date: Apr. 11, 2011

(87) PCT Pub. No.: WO2009/125300
PCT Pub. Date: Oct. 15, 2009

(65) Prior Publication Data
US 2011/0190611 A1    Aug. 4, 2011

Related U.S. Application Data

(60) Provisional application No. 61/042,945, filed on Apr. 7, 2008.

(51) Int. Cl.
*A61M 11/00* (2006.01)
(52) U.S. Cl.
USPC .................. 128/204.23; 128/204.18
(58) Field of Classification Search
USPC .......... 128/204.22, 204.23, 204.18, 205.11, 128/205.24, 205.23, 205.26, 633, 634, 128/205.25
See application file for complete search history.

(56) References Cited

U.S. PATENT DOCUMENTS

| | | | |
|---|---|---|---|
| 4,112,940 A * | 9/1978 | Parkes | 128/205.13 |
| 4,889,116 A | 12/1989 | Taube | 128/204.23 |
| 4,972,842 A * | 11/1990 | Korten et al. | 600/529 |
| 5,315,990 A | 5/1994 | Mondry | 128/205.11 |
| 5,533,512 A | 7/1996 | Novotny et al. | 600/532 |
| 5,682,877 A * | 11/1997 | Mondry | 128/204.23 |
| 5,820,550 A | 10/1998 | Polson et al. | 600/323 |
| 6,532,958 B1 | 3/2003 | Buan et al. | 128/204.23 |
| 6,561,187 B2 | 5/2003 | Schmidt et al. | 128/204.23 |
| 6,671,529 B2 * | 12/2003 | Claure et al. | 600/323 |
| 6,714,805 B2 | 3/2004 | Jeon et al. | 600/323 |
| 7,206,621 B2 | 4/2007 | Aoyagi et al. | 600/323 |
| 2005/0203352 A1 | 9/2005 | Al-Ali et al. | 600/309 |
| 2006/0266355 A1 | 11/2006 | Misholi | 128/204.23 |

FOREIGN PATENT DOCUMENTS

| | | |
|---|---|---|
| JP | 04-210172 | 7/1990 |
| JP | 09-206342 | 1/1996 |
| JP | 2002-11055 | 6/2000 |
| JP | 2002-047003 | 8/2000 |
| JP | 2008-541849 | 5/2006 |
| WO | WO 02/47741 | 6/2002 |

OTHER PUBLICATIONS

"Understanding Pulse Oximetry SpO2 Concepts," published by Phillips Medical Systems, 2003.

(Continued)

*Primary Examiner* — Steven Douglas
(74) *Attorney, Agent, or Firm* — Parker Highlander PLLC

(57) ABSTRACT

The present invention relates to methods and systems for resuscitation of an infant which maintains healthy blood oxygen saturation values in the infant by titration of supplemental oxygen concentrations.

30 Claims, 3 Drawing Sheets

(56) References Cited

OTHER PUBLICATIONS

Chow et al., "Can changes in clinical practice decrease the incidence of severe retinopathy of prematurity in very low birth weight infants?" *Pediatrics*, 111(2): 339-345, 2003.

Dawson et al., "Oxygen saturation and heart rate during delivery room resuscitation of infants <30 weeks' gestation with air or 100% oxygen," *Arch. Dis. Child Fetal Neonatal Ed.*, 94(2): F87-F91, 2009.

Escrig et al., "Achievement of targeted saturation values in extremely low gestational age neonates resuscitated with low or high oxygen concentrations: a prospective, randomized trial," *Pediatrics*, 121(5):875-881, 2008.

International Search Report and Written Opinion issued in PCT/IB2009/005452, dated Oct. 30, 2009.

Kamlin et al., "Oxygen saturation in healthy infants immediately after birth," *J Pediatric.*, 148(5):585-590, 2006.

Mariani et al., "Pre-ductal and post-ductal $O_2$ saturation in healthy term neonates after birth," *J Pediatric.*, 150(4): 418-421, 2007.

Martin et at, "Reevaluating neonatal resuscitation with 100% oxygen," *Am. J. Respiratory and Critical Care Medicine*, 172:1360-1361, 2005.

Rabi et al., "Effect of oxygen exposure during newborn resuscitation on lung injury," abstract presented May 2007.

Rabi et al., "Effect of oxygen exposure during newborn resuscitation on lung injury," abstract presented Jun. 26, 2007.

Rabi et al., "Oxygen saturation trends immediately after birth," *J Pediatric.*, 148(5):590-4, 2006.

Rabi et al., "Room air resuscitation of the depressed newborn: a systematic review and meta-analysis," *Resuscitation*, 72:353-363, 2007.

Saugstad et al., "Take a breath—but do not add oxygen (if not needed)," *Acta Paediatr.*, 96:798-800, 2007.

Dimich et al., "Evaluation of oxygen saturation monitoring by pulse oximetry in neonates in the delivery system," *Can J Anaesth*, 38(8): 985-988, 1991.

Heinonen, "Focus on neonatal resuscitation—NOW," *Acta Paediatrica*, 95:825-829, 2005.

Porter et al., "Evaluation of arterial ocygen saturation of the newborn in the labor and delivery sutie," *J. Perinatology*, 7(4): 337-339, 1987.

Supplementary European Search Report issued European Patent Application No. 09 73 0833, dated Oct. 10, 2012.

Toth et al., "Oxygen saturation in healthy newborn infants immediately after birth measured by pulse oximetry," *Arch Gynecol Obstet*, 266:105-107, 2002.

Wang et al., "Resuscitation of preterm neonates by using room air or 100% oxygen," *Pediatrics*, 121(6): 1083-1088, 2008.

Decision to Grant a Patent issued in Japanese Patent Application No. 2011-503518, dated Jul. 24, 2013.

\* cited by examiner

OXYGENATION PROCEDURES FOR NEWBORNS AND DEVICES FOR USE THEREIN

This application is a national phase application under 35 U.S.C. §371 of International Patent Application No. PCT/IB2009/005452 filed Mar 12, 2009 which claims benefit of priority to U.S. Provisional Application Ser. No. 61/042,945, filed Apr. 7, 2008. The entire text of each of the above-referenced disclosures is specifically incorporated herein by reference without disclaimer.

BACKGROUND OF THE INVENTION

I. Field of the Invention

The present invention relates generally to the field of obstetrics and pediatrics. More particularly, it concerns methods and systems for the titration of the concentration of supplemental oxygen delivered to a preterm infant at the time of birth.

II. Description of Related Art

Every year worldwide, between 5% and 10% of newborn infants require some form of resuscitation. Typically the decision as to whether a newborn needs resuscitation is based on clinical appearance and whether the infant is at high risk (for example, a preterm infant). However, there is currently insufficient evidence to specify the concentration of oxygen ($O_2$) to be used at the initiation of resuscitation. A pulse oximeter is a device that uses a light sensor to continuously measure the amount of oxygen in the blood. Recently, international guidelines have changed to suggest that pulse oximetery may be useful in the delivery room, but there are currently no guidelines on how to use a pulse oximeter in this setting to provide safe oxygen levels to newborns in need.

Moreover, clinicians are becoming increasingly concerned about the dangers of hyperoxia during newborn resuscitation (Saugstad, 2007). Oxygen supplementation may be harmful because $O_2$ free radicals are thought to be involved in the pathogenesis of many neonatal diseases. In newborn infants, hyperoxia may injure the eyes of preterm infants and has been implicated in the development of bronchopulmonary dysplasia. Exposure to hyperoxia at birth may also lead to inflammation, brain injury and perhaps even childhood cancer. Thus, although it is acknowledged that avoiding inappropriately low oxygen levels in the first 10 minutes after birth is important for newborn health, exposure to excessive oxygen can also be harmful. Safe oxygen delivery is thus of critical importantance to the health of neonates.

Studies to date have used static concentrations of oxygen ($O_2$) and focused almost exclusively on term and late-preterm asphyxiated infants. However, these studies do not address the significant issues discussed above. Thus, there is a need to develop a practical, effective and safe approach to delivering oxygen to a preterm infant.

SUMMARY OF THE INVENTION

Thus, in accordance with the present invention, there is provided a method of resuscitating an infant comprising (a) delivering supplemental oxygen to the infant at an oxygen concentration of about 90-100%; (b) monitoring an oxygen saturation value of the preterm infant; and (c) reducing the concentration of supplemental oxygen being delivered by about 20% about every 10 to 20 (e.g., 15) seconds until the oxygen saturation value reaches a desired value. The infant in this regard may be newborn, more specifically, within 10 minutes of age, or 0-20 minutes of age. In particular, the newborn may be a preterm infant. Specifically, the methods and the systems described below may be used in a delivery room for any newborn infant in need thereof. The delivery method of the newborn infant may be vaginal or C-section delivery. Such methods are superior to other methods using static oxygen concentration because they help achieve safe oxygen saturation values while avoiding hyperoxia, which is potentially harmful.

In another embodiment, there is provided a method of resuscitating an infant comprising (a) delivering supplemental oxygen to the preterm infant at an oxygen concentration of about 20-40%; (b) monitoring an oxygen saturation value of the preterm infant; and (c) increasing the concentration of supplemental oxygen being delivered by about 10% to about 20% about every 10 to 20 seconds until the oxygen saturation value reaches a desired value.

In the above methods, the oxygen concentration may be reduced by about 20%, and/or reduced occurs about every 15 seconds. The infant in this regard may be newborn, more specifically, within about 0-20 minutes of age. Specifically, the methods and the systems described below may be used in a delivery room for a newborn infant. The delivery method of the newborn infant may be vaginal or C-section.

In particular aspects, for safe delivery of oxygen to an infant, the desired oxygen saturation values may reflect the time-dependent pattern of oxygen saturation values observed in healthy newborn infants, who may not require supplemental oxygen. More specifically, the desired value may be approximately 73% to 81% at 1 minute of age of the infant, approximately 77% to 82% at 2 minutes of age, approximately 78% to 87% at 3 minutes of age, approximately 79% to 91% at 4 minutes of age, approximately 80% to 95% at 5 minutes of age, approximately 80% to 93% at 6 minutes of age, approximately 82% to 93% at 7 minutes of age, 83% to 95% at 8 minutes of age, approximately 87% to 95% at 9 minutes of age, or approximately 91% to 95% at 10 minutes of age.

In a certain embodiment, the oxygen saturation may be monitored by an oxygen saturation monitor, such as a pulse oximeter. The pulse oximeter may be placed on a wrist (more particularly, right wrist) of the infant, and may use the maximum sensitivity setting available on that particular model. The oxygen saturation value may be monitored using the shortest averaging time available on that model, usually this a two second averaging time, to obtain a continuous time-dependent pattern of the infant's oxygen saturation.

In a further embodiment, the supplemental oxygen may be delivered by an anaesthesia bag coupled to a face mask or an endotracheal tube, a ventilator or a continuous positive airway pressure system. In a still further embodiment, the supplemental oxygen may be delivered at an oxygen concentration of at least about 21%, about 29%, about 33%, about 46%, or about 63%, or at about 20% to about 65%.

The invention is also directed, in certain embodiments, to a system for resuscitation of a infant comprising (a) a supplemental oxygen delivery module configured to deliver supplemental oxygen to the infant in accordance with the methods described above; (b) an oxygen saturation monitor for monitoring an oxygen saturation value of the infant; (c) a display comparing a time-dependent oxygen saturation values of the infant following birth with the desired value; (d) a warning system to indicate whether the oxygen saturation value disagrees with the desired value; an (e) a control module to adjust concentration of the supplemental oxygen. The supplemental oxygen delivery module may comprise a flow meter to control the rate of flow of the gases used in resuscitation, and oxygen blender. The display may further include a visual graph comprising the upper and lower limits of the desired oxygen saturation value, which may vary over time and mimic a normal range of oxygen saturation values observed in healthy newborn infants. The concentration of the supplemental oxygen may be adjusted based on the magnitude and direction of the difference between the observed oxygen saturation value with the desired value. At the time of birth of the infant, a timer on the display may be started and will display the infants age in minutes and seconds. The oxygen saturation monitor may be started immediately prior to delivery or at the time of delivery, and will continuously send data to the control module in real-time.

A "preterm infant" as used herein, refers to an infant born prior to 37 weeks of gestation.

"Supplemental oxygen" as used herein, refers to oxygen delivered to a human in addition to the oxygen received by the subject through the inspiration of room air or ambient air. Because room air contains some oxygen, the supplemental oxygen may be provided in addition to the oxygen that would normally be inspired by the subject.

An "oxygen saturation value" as used herein, refers to oxygen saturation as commonly measured in the percentage of oxygen-saturated hemoglobin ($SpO_2$) by an oxygen saturation monitor or sensor, e.g., a pulse oximeter, although it can also refer to any suitable measurement for determining the level of oxygenation in a human subject's blood, either non-invasive or invasive. For example, it will be understood that an oxygen saturation value can also by obtained from a sample of blood using a co-oximeter. Furthermore, an oxygen saturation value can also be inferred based on partial pressures of oxygen.

"Titration" and "titrating" refer to changing of the supplemental oxygen concentration over time by either decreasing or increasing the inspired concentration of oxygen using an oxygen blender. Currently there are no specific recommendations from Canadian or American committees that produce resuscitation guidelines in newborns regarding frequency of titration, amount by which to titrate oxygen or appropriate starting concentration of oxygen.

"Continuous" and "continuously" as used herein (when referring to the monitoring of oxygen saturation values), mean that the oxygen saturation value will be measured without cessation or at discrete intervals (fixed or variable) that are sufficiently small to provide the advantages of the invention. Specifically, the sampling intervals will be less than about sixteen second, and in particular, at about every two seconds.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" or "approximately" is used to indicate that a value includes the standard deviation of error for the system or method being employed to determine the value, and may include 5-10% of the stated value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

I. The Present Invention

Figure 1:
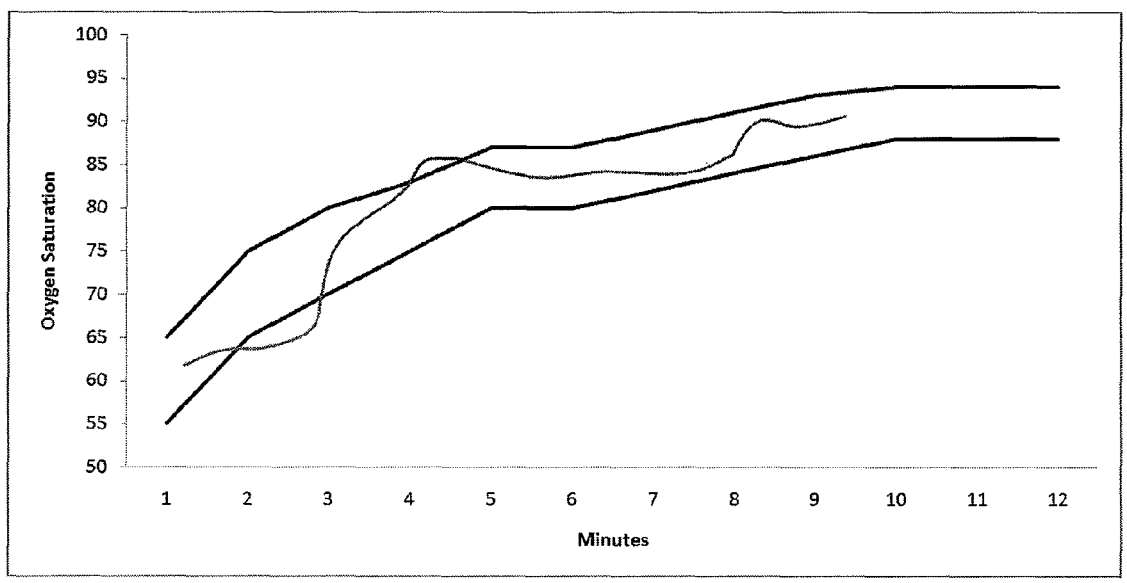
FIG. 1. An example of a graph of oxygen saturation values of an infant compared with an approximation of an appropriate oxygen saturation target range over time following birth of the infant in accordance with the method of the invention.

As discussed above, over the past 10 years, there has been increasing concern about the potential harmful effects of oxygen use during newborn resuscitation. Specifically, several studies have consistently demonstrated that delivery room resuscitation of term infants with 100% oxygen leads to worse outcomes compared to infants resuscitated with 21% oxygen (room air). When the results of these studies are combined, using a technique called a meta-analysis, it becomes apparent that the mortality rate is dramatically increased in infants resuscitated with 100% oxygen compared to those receiving room air (Rabi et al., 2007). All of these studies were performed in term or near-term asphyxiated infants and used static concentrations of oxygen. This is important to note, since term infants should have healthy lungs, and therefore, supplemental oxygen may not be needed. However, preterm infants often have pre-existing lung pathology which may impair the absorption of oxygen. Hence, the use of room air during the resuscitation of preterm infants may be inappropriate as an inadequate amount of oxygen may be transferred to the infant's blood from his/her lungs. Inappropriately low blood oxygen levels are associated with injury of several organs including the brain, heart, liver, gut and kidneys.

Recent studies have prompted the major North American institutions that author newborn resuscitation guidelines to change their recommendations regarding oxygen. Previously, the guidelines universally stated that all newborns should be resuscitated with static concentrations of 100% oxygen. The latest guidelines from the Neonatal Resuscitation Program, under the umbrella of the American Academy of Pediatrics, changed its recommendations to state that using concentrations of oxygen less than 100% may be appropriate in certain situations. The Canadian Pediatric Society was more prescriptive and stated that newborn resuscitation should begin with room air and that, furthermore, supplemental oxygen should not be given until the infant is 90 seconds of age, assuming that the heart rate is greater than 100 beats per minute. However, these guidelines do not specify the method of determining the proper concentration of oxygen required to meet the physiologic needs of the infants while avoiding the dangers of hypoxia and hyperoxia.

Here, the inventors provide, for the first time, methods and systems to deliver supplemental oxygen to infants, including those that are preterm, by titrating the concentration of the supplemental oxygen, which may be combined with monitoring of the infant's oxygen saturation value, to achieve improved results in terms of oxygenation and avoidance of toxicity.

II. Supplemental Oxygen Delivery

The world's leading authority on oxygen use during newborn resuscitation has repeatedly asserted that, at the current time, the best strategy for newborn resuscitation is for the physician to deliver oxygen in an attempt to mimic the pattern of normal oxygen saturations observed in healthy newborns. However, it is important to consider that oxygen saturations in the normal newborn change continuously during the first 10 minutes after birth. Furthermore, one needs to consider both the upper and lower limit of oxygen saturations observed in healthy newborns at each minute (20 target points in total).

The present invention, in certain embodiments, provides methods and systems of resuscitating an infant by titrating supplemental oxygen concentration delivered to the infant and applying the desired oxygen saturation value or range to help guide the delivery of oxygen. An oxygen saturation monitor, such as a pulse oximeter, may be used to continuously monitor oxygen saturation values of an infant to guide the supplemental oxygen delivery to mimic a target range of oxygen saturation in healthy infants in accordance with aspects of the invention.

In certain aspects of the present invention, it is contemplated that the desired value or target range of oxygen saturation for a preterm infant could be set at about 80 to about 98%, about 85% to about 95%, about 85% to about 92%, about 88% to about 90%, or any intermediate range of the foregoing. These desired values are set as a reasonable safety zone for the great majority of infants for delivering supplemental oxygen. An example of a time-dependent pattern of oxygen saturation value in the health newborn infant may be depicted as in FIG. 1. In particular aspects, the desired value may be a time-dependent pattern of an oxygen saturation value in a healthy newborn infant, who may not require supplemental oxygen. More specifically, in the infant, the desired value may be approximately 73% to 81% at 1 minute of age of the preterm infant, approximately 77% to 82% at 2 minutes of age, approximately 78% to 87% at 3 minutes of age, approximately 79% to 91% at 4 minutes of age, approximately 80% to 95% at 5 minutes of age, approximately 80% to 93% at 6 minutes of age, approximately 82% to 93% at 7 minutes of age, 83% to 95% at 8 minutes of age, approximately 87% to 95% at 9 minutes of age, or approximately 91% to 95% at 10 minutes of age.

In certain embodiments, if the infant's oxygen saturation is outside the desired value or target range comprising an upper limit and a lower limit as exemplified above, it could trigger an intervention to adjust supplemental oxygen delivery. It may be to observe, give or withdraw oxygen. Optionally but not necessarily, the infant may be monitored closely for need, efficacy and side-effect (oxygen toxicity, hypoxemia). Oxygen supplementation could be delivered via a bag and mask resuscitator, endotracheal tube placement with subsequent positive pressure breaths delivered via a manual bagging unit or mechanical ventilator, a continuous positive airway device or via free-flow oxygen blown at the infant's face. The upper limit is the oxygen saturation within which it could be reasonably suggested the infant's oxygen saturation value is not too high. Once the infant's saturation value is above the upper limit, the person performing resuscitation may need to reduce the concentration of delivered oxygen. Once below a lower limit, the person performing resuscitation may need to increase the concentration of delivered oxygen. Some infants may have a target range which is prescribed outside the exemplified 85-95% range. Examples of such infants are: infants at risk for or with pulmonary hypertension such as may results from pulmonary hypoplasia, congenital diaphragmatic hernia or meconium aspiration syndrome or in the case of certain cyanotic congenital heart disease or in the case of certain blood dyscrasias. In such instances, it may be appropriate to specify different oxygen saturation target ranges and alarm values which are specific to them.

Regarding strategy, once the infant reaches the target oxygen saturation range, the user may make smaller adjustments to the oxygen concentration given, i.e., the user can hold at the necessary concentration given or can make finer adjustments to keep in range—basically this is up to the user. It is at the discretion of the user to monitor the infant while in the delivery room and ensure the infant has a target blood oxygen level, no matter how long this takes, for example, at least 10 minutes, at least 30 minutes, at least 1 h, at least 4 h, at least 8 h, at least 12 h, in the delivery room.

III. System

Figure 2:
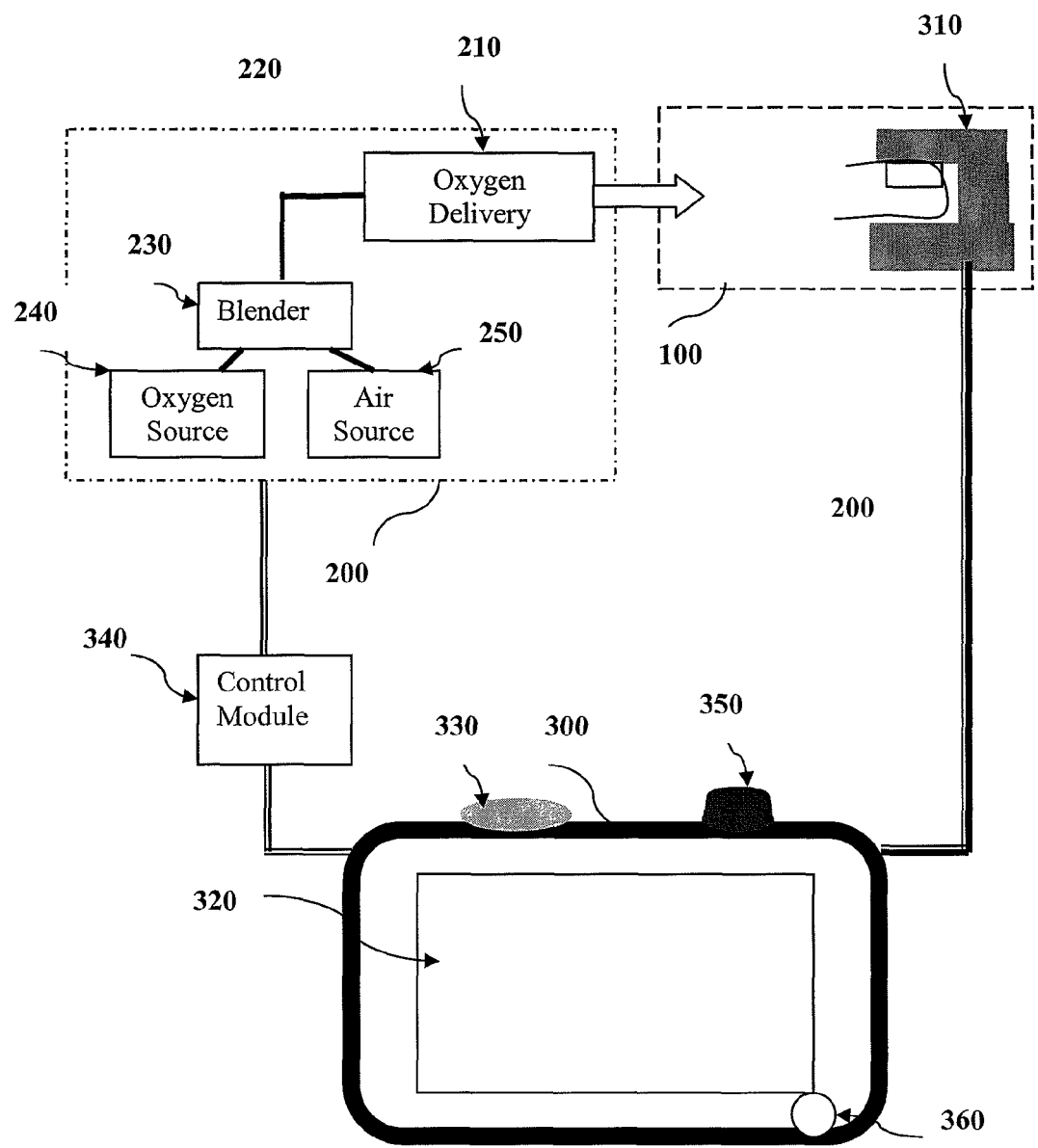
FIG. 2. An embodiment of a system for resuscitation of an infant in accordance with certain aspects of the invention.

One specific embodiment of a supplemental oxygen delivery system is depicted in FIG. 2. This system may include an oxygen delivery module 200 configured to deliver supplemental oxygen in accordance with the methods described above, a display 300, a audible warning system 330 and a visual warning system 320, and a control module 340. The system may be a stand alone system coupled to an oxygen monitor 310, further comprise oxygen monitor 310, or be part of oxygen monitor 310. The control module 340 may comprise an automated system that monitors and adjusts independently, or it may comprise a manual control to be adjusted by the operator based on the operator's evaluation of the system's and infant's conditions.

Oxygen could be delivered to an infant 100 from the oxygen delivery module 200, which may comprise an oxygen delivery device 210. The oxygen delivery device 210 can take the form of any device to provide supplemental oxygen to an infant while not preventing the infant from also inspiring room or ambient air in addition to the supplemental oxygen from an oxygen source. Examples of such a supplemental oxygen delivery device 210 include, but are not limited to an anaesthesia (or T-piece) bag, a ventilator, a bag valve mask (also known as Ambu bag), a tracheal catheter, a nasal mask configured to use with Continuous Positive Airway Pressure (CPAP) systems, etc.

To practice the titration methods described above, the oxygen delivery module may comprise an oxygen source 240 and an air source 250, both of which are coupled to a blender or mixer 230, to deliver supplemental oxygen to the preterm infant 100 in accordance with certain aspects of the present invention. The blender 230 may be configured to provide controllable delivery of supplemental oxygen at varying concentrations, for example, starting at an oxygen concentration of about 100% and reducing the concentration of supplemental oxygen being delivered by about 10% to about 20% about every 10 to 20 (e.g., 15) seconds until the oxygen saturation value reaches a desired value, or starting at an oxygen concentration of about 21% and increasing the concentration of supplemental oxygen being delivered by about 10% to about 20% about every 10 to 20 (e.g., 15) seconds until the oxygen saturation value reaches a desired value. A flow meter may be positioned between the blender or mixer 230 and the oxygen delivery device 210, which comprises valve that lets the user adjust the flow rate in liters/min of the gas mixture being delivered to the patient, with a particular mode being 6-8 liters/min.

Oxygen source 240 could be an oxygen concentrator, membrane separator, high pressure cylinder or liquid oxygen dewar. This could also include any portable versions of oxygen sources. Other potential sources of oxygen gas suitable for providing supplemental oxygen to an infant may be created in the future and should be considered as being functional with the described invention. An alternative embodiment may be provided that oxygen source 240 and air source 250 are a high concentration oxygen source and a low concentration oxygen source, respectively. Furthermore, oxygen source 240 or air source 250 may comprise a valve or the like to control the flow rate of each gas to the oxygen delivery device 210 to titrate or control oxygen concentration.

The present methods or system include an oxygen saturation monitor 310 for monitoring the oxygen saturation value of the infant 100. One particular oxygen monitor is a non-invasive sensor such as a pulse oximeter. As used herein, the term "pulse oximeter" will include both the optical sensor and the circuitry used to determine oxygen saturation levels using the optical sensor. One example of a suitable pulse oximeter is a conventional two-color, OEM-II oximeter module, from Nonin Medical Inc. of Plymouth, Minn., that can measure the percentage of oxygen-saturated hemoglobin, $SpO_2$, in the blood stream in vivo.

While the pulse oximeter is one particular example of a non-invasive oxygen monitor, it should be understood that any oxygen sensor, invasive or non-invasive, useful for determining oxygen content levels (preferably continuously) could be used in connection with the present invention. It should also be apparent to those skilled in the art that technologies on the horizon, such as an implantable, micro-electromechanical (MEMS) gas analyzer, may provide the oxygen content information needed by the control module 330. Furthermore, there may be improvements in pulse oximetry technology, such as the ability to determine the level of carboxyhemoglobin in the blood that may be useful for the described invention. Use of these new oxygen content technologies in oxygen conservers for oxygen therapy should be considered to lie within the scope of the systems and methods of the present invention provided they have the ability to provide suitable oxygen saturation measurements. The pulse oximeter 310 may be used in the maximum sensitivity setting and maximum detection frequency (shortest averaging time, e.g., 2 seconds) according to manufacturer's instructions in specific embodiments.

One suitable monitor includes a sensor control module and a probe typically mounted or attached to infant 100 by some suitable technique. A particular embodiment of the pulse oximeter 310 comprises may be a transmitting probe that attaches to infant 100's palm of its right hand specifically or across its right wrist properly (preductal), while it is believed that such preductal measurement gives a more accurate representation of brain oxygenation compared with postductal measurement (for example, attach site is left hand or wrist, left/right foot or toe). Alternative embodiments may also employ probes that attach elsewhere on the body, for example, forehead, to also supply preductal oxygen saturations. Alternative embodiments may also employ probes that attach to other locations on the body, for example, postductal, and accordingly the desired value to mimic for oxygen delivery will be appropriate target ranges of postductal $SpO_2$ in healthy infants.

After placing a probe on the infant 100, light containing both red and infrared wavelengths may be passed from one side to the other. Changing absorbance of each of the two wavelengths may be measured, allowing determination of the absorbance due to the pulsing arterial alone, excluding venous, skin, bone, muscle and fat. Based upon the ratio of changing absorbance of the red and infrared light caused by the difference in color between oxygen-bound (bright red) and oxygen unbound (dark red or blue, in severe cases) hemoglobin, a measure of oxygenation (the percent of hemoglobin molecules bound with oxygen molecules) or oxygen saturation value can be made.

The information from the oxygen saturation monitor 310 may be sent to a display 320 and/or a control module 330 for use in executing the methods according to the present invention, for example, oxygen saturation monitor 310 may be coupled to other components of the system by a cable or any form which is configured for sending oxygen saturation measurement information. It may be provided, but not required, that oxygen saturation monitor 310 provides a signal in the form of oxygen saturation in percent.

Display 300 (e.g., an LCD display) may be configured to compare time-dependent oxygen saturation values of the preterm infant 100 after birth with the desired value of health infants such as shown in FIG. 1. Display 300 may further comprise a visual graph 320 comprising a time-dependent pattern of the desired value with an upper limit and a lower limit, which may vary over time and mimic a normal range of oxygen saturations in a healthy newborn infant, and a graph of oxygen saturations versus time of the preterm infant 100 that is populated in real time for comparison. At the time of birth of the infant 100, a timer start/stop switch 350 comprised in the system may be initiated, with an image of a timer (Apgar clock) 360 on the display 320 started and the oxygen saturation monitor 310 having started to monitor oxygen saturation of infant 100 and send data to the system. For example, an Apgar clock 360 may be shown on display 300; a button 350 on the system may be pushed at the time of birth to start the clock 360 and initiate the streaming of data from the pulse oximeter 310. Then a display will appear in a graph format showing appropriate oxygen ranges (blood level oxygen levels) at every minute following birth. This is what the physician should target. If the blood levels are too low, the data sent from pulse oximeter 310 will feed back to the control module 330 to signal the person performing the resuscitation to use the oxygen delivery module 200 to increase oxygen delivery and vice versa to maintain within the range in accordance with the titration method described above.

A warning system 330 comprising an auditory alarm either would warn a physician if the baby's oxygen levels are outside the appropriate range. Furthermore, oxygen saturation values outside of the appropriate range would appear in a different color than the in range values, thereby providing a visual alarm on the LCD display 320. For example, data points below the lower limit of normal will be blue in color, those within the target range will be green and readings above the upper limit of normal saturations will appear red. Audible alarms 330 may also signal low readings (low frequency alarm) and high readings (high frequency alarm). By using different frequencies of alarms for low and high oxygen saturation values, the person performing the resuscitation should be able to determine if the oxygen saturations are above or below the desired range without looking at the display.

This graphical format is particularly informative because it not only indicates if the infant's oxygen saturation is above, within or below the range, but also gives a visual indication of the magnitude of how far out of range the oxygen saturations are. This provides information to a user to help guide how aggressive they should be in increasing or decreasing the oxygen concentration. When infant 100 require aggressive resuscitation, it may be given 100% oxygen and this procedure could include chest compression if indicated.

The user may have the option of adjusting the time resolution of the graph 320 to display more or less detail; a higher resolution would show greater detail in the oxygen curve but require the screen to scroll horizontally in order to accommodate the entire duration of the resuscitation.

The heart rate and pulsatility index may be transferred from the pulse oximeter 310 and displayed on the display 300 in real time. The pulsatility index gives information regarding the strength of the signal. Taken together, the heart rate and pulsatility index give valuable information regarding the validity of the data. In times where the pulsatility index is below a predetermined cutoff value, affected data will not be presented on the graph as it might be misleading.

It will be recognized by those skilled in the art that the appropriate upper and lower oxygen saturation limits may be adjusted as further research is conducted. Therefore, the saturation limits presented on the system will be adjustable via software updates.

IV. EXAMPLES

The following examples are included to further illustrate various aspects of the invention. It should be appreciated by those of skill in the art that the techniques disclosed in the examples that follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Room Air Versus Oxygen Administration During Resuscitation of Preterm Infants OBJECTIVE: Compare three $O_2$ delivery strategies to determine which approach is most effective at remaining within a target transcutaneous oxygen saturation ($SpO_2$) range of 85 to 92% and determine if using a protocol to titrate $FiO_2$ (fraction of inspired oxygen in a gas mixture, used herein as concentration of supplemental oxygen) during resuscitation of preterm infants is feasible.

DESIGN/METHODS: Blinded, randomized control trial of delivery room resuscitation in infants 32 weeks gestation comparing three $O_2$ strategies. The High $O_2$ Burden (HOB) group received a static concentration of 100% $O_2$. In the Moderate $O_2$ Burden (MOB) and Low $O_2$ Burden (LOB) groups, resuscitation started with 100% and 21% $O_2$, respectively. The inspired oxygen concentration was adjusted by 20% every 15 seconds in the MOB and LOB groups until the target $SpO_2$ range of 85% to 92% was reached. $SpO_2$ measurements were recorded every 2 seconds from the right wrist (pre-ductal) and the maximum sensitivity setting of the pulse oximetry was used. An anesthesia monitor continuously measured and recorded respiratory parameters including the peak inspiratory pressure, respiratory rate, end-tidal $CO_2$ and inspired $O_2$ concentration.

RESULTS: There were three sets of preterm infants that were part of this study. The LOB (low oxygen burden group—resuscitation began with room air given followed by a 20% increase every 15 sec as long as the oxygen saturation was less than 85%), MOB (high oxygen burden group—resuscitation began with 100% oxygen given and decreased 20% every 15 sec as long as the oxygen saturation was greater than 92%) and HOB (high oxygen burden group—100% oxygen given continuously). The inventors enrolled 106 preterm infants (<32 weeks gestation) (LOB=34, MOB=34, LOB=38). The three groups had similar baseline characteristics. The mean proportion of resuscitation time spent in the target $SpO_2$ range (85-92%) was 11%, 21% and 16% for the HOB, MOB and LOB groups, respectively shown in Table 1 (CI: confidence interval). The MOB group spent the most amount of time in the target range (21%) compared to the other two groups. The MOB group spent nearly twice as long in this target oxygen range as the HOB group. Note that the mean proportion of time on target is significantly different (P=0.006) among the three groups and that this is attributable to the difference between the MOB and HOB groups.

TABLE 1

MEAN PROPORTION OF TIME IN TARGET BY GROUP

| | Mean | CI Lower | CI Upper |
|---|---|---|---|
| Low | 0.16 | 0.13 | 0.20 |
| Moderate | 0.21 | 0.16 | 0.26 |
| High | 0.11 | 0.09 | 0.14 |

There was a significant effect of oxygen strategy (p=0.006) on time spent in the target $SpO_2$ range, with the MOB group spending the greatest proportion of time in-range. The LOB group spent the greatest proportion of time (61%) below range (p<0.001) (Table 2) and the HOB group spent the greatest proportion of time (49%) above range (p<0.001) (Table 3), so both the LOB and HOB protocols may be inferior to the MOB protocol. Note that the mean proportion of time below or above target is significantly different (P<0.001) among the three groups.

TABLE 2

MEAN PROPORTION OF TIME BELOW TARGET BY GROUP

| | Mean | CI Lower | CI Upper |
|---|---|---|---|
| Low | 0.61 | 0.55 | 0.67 |
| Moderate | 0.51 | 0.46 | 0.56 |
| High | 0.40 | 0.34 | 0.45 |

TABLE 3

| MEAN PROPORTION OF TIME ABOVE TARGET BY GROUP | | | |
|---|---|---|---|
| | Mean | CI Lower | CI Upper |
| Low | 0.23 | 0.18 | 0.27 |
| Moderate | 0.28 | 0.23 | 0.33 |
| High | 0.49 | 0.42 | 0.56 |

Although infants were randomized to one of the three different treatment groups, it is important to assess the overall exposure to oxygen. The treatment allocation dealt with starting the child on a certain level of oxygen, but exposure to it is adjusted as the child needs it during resuscitation and hence the total exposure can end up being similar for children in different treatment groups. The inventors assessed total oxygen exposure via the area under the oxygen vs time curve. There is a significant difference between the three treatment groups for area under the curve (P-value=0.044). This data support the conclusion that while the LOB and MOB groups received similar total amounts of oxygen (they had similar oxygen exposure), the MOB group reached and stayed in the target region the longest, while this wasn't observed with the LOB group (Table 1). This illustrates that the protocol used for titrating oxygen concentration is important in reaching a target oxygen saturation. It is important to consider not only the amount of oxygen that is delivered to an infant, but also the protocol used to guide the titration of oxygen.

Figure 3:
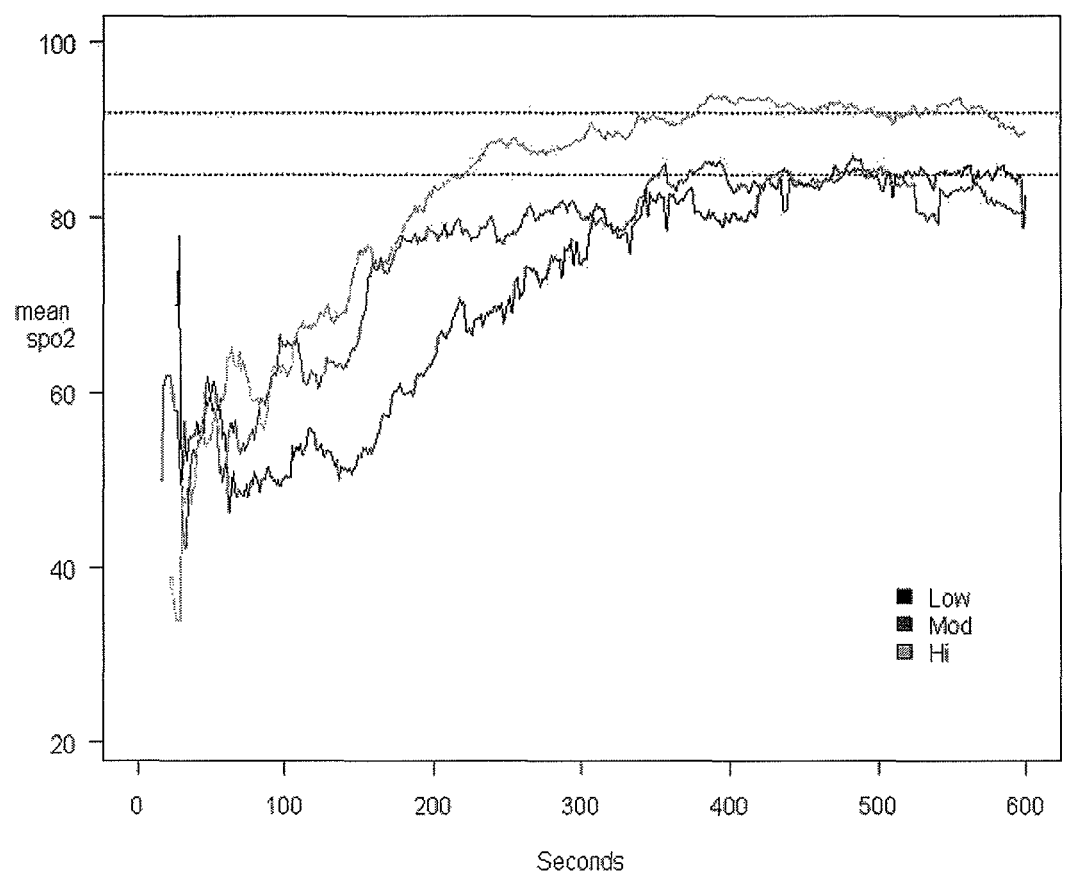
FIG. 3. Comparison of low (LOB; darkest), medium (MOB; intermediate) and high oxygen burden (HOB; lightest) groups. X-axis indicates the time immediately after birth in seconds, x=0 means the time of birth; the y-axis shows the $SpO_2$ measured by the pulse oximeter.

FIG. 3 shows that the MOB and HOB groups took approximately 5 minutes immediately after birth to reach the target range (the x-axis indicate the time immediately after birth, x=0 means the time of birth; the y-axis shows the $SpO_2$ measured by pulse oximetry). This shows that the protocol for oxygen administration was favorable because these groups didn't reach the target range (85-92%, shown by the shaded area) too quickly nor did they take too long. Note that the target oxygen saturation range in this study does not reflect the normal pattern of oxygen saturation observed in healthy newborns. However, it appears that the oxygen saturations of infants in the MOB group, compared to the LOB and HOB groups, may be most closely approximated to the pattern of oxygen saturations observed in healthy infants.

As shown in Table 4 below, the duration of resuscitation (seconds) is not significantly different (ANOVA=NS) among the three groups.

TABLE 4

| MEAN DURATION OF RESUSCITATION BY GROUP | | | |
|---|---|---|---|
| | Mean | CI Lower | CI Upper |
| Low | 677.00 | 587.76 | 766.24 |
| Moderate | 665.00 | 548.59 | 781.41 |
| High | 590.62 | 515.06 | 666.19 |

The mean inspired $O_2$ concentrations at the end of resuscitation for the HOB, MOB and LOB groups were 100%, 33% and 36%, respectively. There were no significant differences between the three groups for the peak inspiratory pressure, rate of positive pressure breaths or end tidal $CO_2$ concentration.

CONCLUSIONS: In this study of preterm infants, the strategy of starting resuscitation with 100% $O_2$ followed by titration of the inspired oxygen concentration was most effective at maintaining the $SpO_2$ in the target range of 85-92%. Given that preterm infants are at high risk for surfactant deficiency, room air may not be an appropriate choice for initiating resuscitation in this population. This study also showed that pulse oximetry can be used to guide titration of the inspired $O_2$ concentration during delivery room resuscitation of preterm infants.

The study found that infants in the Moderate Oxygen Burden (MOB) group spent the most time in the target oxygen saturation range of 85 to 92%. This is the group that started at 100% oxygen and had subsequent titration of the oxygen concentration. This is important for 3 reasons. First, the results were statistically significant and the study was methodologically very strong. Second, there were no significant differences between the total exposure to oxygen between the LOB group (started at 21% oxygen) and the MOB group. Despite this, the MOB group still spent more time in the target range. In other words, both the MOB and LOB groups had similar oxygen exposures but the MOB group spent the most time in the target range (approximately 25% more time in target range than the LOB group). This implies that the choices made very early in the resuscitation process (i.e., the first minute) have significant effects on how well we can keep the infant in the safe target range. Third, infants in the LOB and MOB groups were receiving oxygen concentrations of 36% and 33%, respectively, at the end of the resuscitation. This shows that using a static concentration of 21% oxygen (as has been the case in all previous related studies) is not appropriate since even at the end of resuscitation (typically when a baby is at his/her most stable) babies are, on average, needing more that 21% oxygen.

Therefore, these results have shown that a better strategy for resuscitating preterm babies involves titrating the amount of oxygen that they receive as opposed to giving them a static oxygen concentration. Regarding the target range for titration, this study used a simple static target of 85-92% and showed that the oxygen concentration can be safely and effectively titrated to reach a target during resuscitation. It has been suggested that the 'best' target is likely the pattern of oxygen saturations observed in healthy infants (Rabi et al., 2006; Mariani et al., 2007) which changes on a minute by minute basis.

* * *

All of the methods and/or systems disclosed and claimed herein can be made and executed without undue experimentation in light of the present disclosure. While the methods and/or systems of this invention have been described in terms of particular embodiments, it will be apparent to those of skill in the art that variations may be applied to the methods and/or systems in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

V. References

The following references, to the extent that they provide exemplary procedural or other details supplementary to those set forth herein, are specifically incorporated herein by reference:

Mariani et al., *J Pediatr.*, 150(4):418-21, 2007
Rabi et al., *J Pediatr.*, 148(5):590-4, 2006
Rabi et al., *Resuscitation*, 72(3):353-63, 2007
Saugstad, *Acta Paediatr.*, 96(6):798-800, 2007

The invention claimed is:

1. A method of resuscitating an infant comprising:
   (a) delivering supplemental oxygen to said infant at an oxygen concentration of about 20-40%;

(b) monitoring an oxygen saturation value of said infant; and (c) increasing the concentration of supplemental oxygen being delivered by about 10% to about 20% about every 10 to 20 seconds until said oxygen saturation value reaches a desired value.

2. A system for resuscitation of an infant comprising: (a) a supplemental oxygen delivery module configured to deliver supplemental oxygen to said infant in accordance with the method of claim 1; (b) an oxygen monitor for monitoring an oxygen saturation value of said infant; (c) a display comparing a time-dependent oxygen saturation value of said infant following birth with said desired value; (d) a warning system to indicate whether said oxygen saturation value disagree with said desired value; and (e) a control module to adjust concentration of said supplemental oxygen.

3. The system of claim 2, wherein the display comprises a visual graph comprising said desired value with an upper and a lower limit.

4. The system of claim 2, wherein concentration of said supplemental oxygen is adjusted based on the difference between said oxygen saturation values with said desired value.

5. The system of claim 2, wherein at time of birth of said infant, an image of a timer comprised in the display is started, and the oxygen saturation monitor is started to monitor said oxygen saturation value to send to said control module.

6. The method of claim 1, wherein said newborn infant is preterm.

7. The method of claim 1, wherein said newborn infant is within about 0-20 minutes of age.

8. The method of claim 1, wherein said desired value is approximately 73% to 81% at 1 minute of age.

9. The method of claim 1, wherein said desired value is approximately 77% to 82% at 2 minutes of age.

10. The method of claim 1, wherein said desired value is approximately 78% to 87% at 3 minutes of age.

11. The method of claim 1, wherein said desired value is approximately 79% to 91% at 4 minutes of age.

12. The method of claim 1, wherein said desired oxygen value is approximately 80% to 95% at 5 minutes of age.

13. The method of claim 1, wherein said desired value is approximately 80% to 93% at 6 minutes of age.

14. The method of claim 1, wherein said desired value is approximately 82% to 93% at 7 minutes of age.

15. The method of claim 1, wherein said desired value is approximately 83% to 95% at 8 minutes of age.

16. The method of claim 1, wherein said desired value is approximately 87% to 95% at 9 minutes of age.

17. The method of claim 1, wherein said desired value is approximately 91% to 95% at 10 minutes of age.

18. The method of claim 1, wherein said desired value is a time-dependent pattern of an oxygen saturation value in healthy newborn infant not requiring supplemental oxygen in the delivery room.

19. The method of claim 1, wherein said oxygen saturation value is monitored by a pulse oximeter.

20. The method of claim 18, wherein said pulse oximeter is placed on a right wrist of said infant.

21. The method of claim 18, wherein said oxygen saturation value is monitored using a two-second averaging time.

22. The method of claim 18, wherein said pulse oximeter uses the maximum sensitivity setting available on the pulse oximeter.

23. The method of claim 1, wherein said supplemental oxygen is delivered by an anaesthesia bag coupled to a face mask or an endotracheal tube.

24. The method of claim 1, wherein said supplemental oxygen is delivered by a mechanical ventilator.

25. The method of claim 1, wherein said supplemental oxygen is delivered by a continuous positive airway pressure system.

26. The method of claim 1, wherein said supplemental oxygen is delivered at an oxygen concentration of at least about 21%.

27. The method of claim 1, wherein said supplemental oxygen is delivered at an oxygen concentration of at least about 29%.

28. The method of claim 1, wherein said supplemental oxygen is delivered at an oxygen concentration of at least about 33%.

29. The method of claim 1, wherein said supplemental oxygen is delivered at an oxygen concentration of at least about 46%.

30. The method of claim 1, wherein said supplemental oxygen is delivered at an oxygen concentration of at least about 63%

* * * * *

UNITED STATES PATENT AND TRADEMARK OFFICE
CERTIFICATE OF CORRECTION

| | |
|---|---|
| PATENT NO. | : 8,689,788 B2 |
| APPLICATION NO. | : 12/937180 |
| DATED | : April 8, 2014 |
| INVENTOR(S) | : Yacov Rabi |

Page 1 of 1

It is certified that error appears in the above-identified patent and that said Letters Patent is hereby corrected as shown below:

In the Claims:

In claim 30, column 14, line 43, delete "about 63%" and replace with --about 63%.-- therefor.

Signed and Sealed this
Eighth Day of July, 2014

Michelle K. Lee
*Deputy Director of the United States Patent and Trademark Office*